United States Patent [19]
Walker

[11] 4,114,455
[45] Sep. 19, 1978

[54] ULTRASONIC VELOCITY MEASURING METHOD AND APPARATUS

[75] Inventor: Philip A. Walker, Trumbull, Conn.

[73] Assignee: Krautkramer-Branson, Incorporated, Stratford, Conn.

[21] Appl. No.: 840,592

[22] Filed: Oct. 7, 1977

[51] Int. Cl.² ............................................. G01N 29/00
[52] U.S. Cl. ......................................... 73/597; 73/629
[58] Field of Search .................. 73/597, 611, 627, 629

[56] References Cited

U.S. PATENT DOCUMENTS

| | | | |
|---|---|---|---|
| 3,848,460 | 11/1974 | Bantz et al. | 73/597 |
| 3,985,022 | 10/1976 | Dileo et al. | 73/629 |
| 3,994,154 | 11/1976 | Niklas | 73/597 |

Primary Examiner—Stephen A. Kreitman
Attorney, Agent, or Firm—Ervin B. Steinberg; Philip J. Feig

[57] ABSTRACT

In a pulse echo ultrasonic velocity measuring apparatus timing gate signals corresponding to the transit time of search signals traveling through a workpiece are generated. The quantity of fixed frequency pulses occurring during successive timing gate signals is counted and accumulated using time interval averaging techniques until a predetermined quantity of pulses commensurate with the thickness of the workpieces is accumulated. Concurrently, the quantity of search signals required to accumulate the predetermined quantity of pulses is counted. The quantity of search signals counted is commensurate with the acoustic velocity of the workpiece.

22 Claims, 1 Drawing Figure

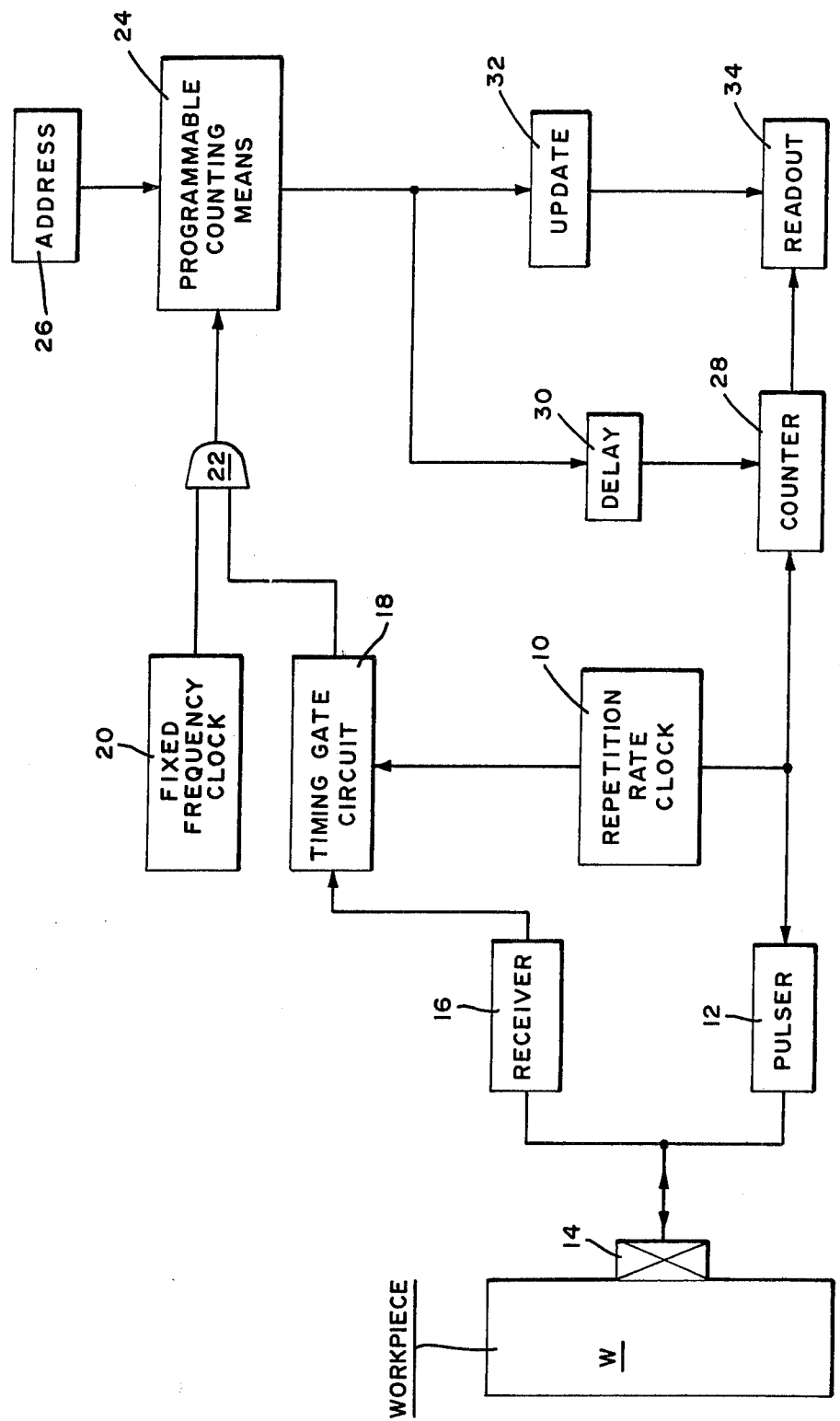

ULTRASONIC VELOCITY MEASURING METHOD AND APPARATUS

BRIEF SUMMARY OF THE INVENTION

This invention refers to an ultrasonic velocity measuring arrangement exhibiting improved stability and calibration adaptability. More specifically, this invention concerns an ultrasonic pulse-echo velocity measuring method and apparatus comprising a time interval averaging circuit in combination with a programmable means for counting and accumulating a predetermined quantity of pulses while concurrently counting the number of measuring cycles required to accumulate the predetermined quantity. The quantity of measuring cycles is commensurate with the acoustic velocity of the workpiece.

Measuring the acoustic velocity of a workpiece by ultrasonic energy is well known. The general measurement method comprises the steps of coupling an ultrasonic transmit-receive probe to the surface of the workpiece, transmitting an ultrasonic search pulse into the workpiece and subsequently receiving echo responsive pulses produced as a respective search pulse encounters the entrant surface and the rear wall of the workpiece. A timing gate circuit is started responsive to the receipt of the entrant surface responsive echo pulse and is terminated upon receipt of the rear wall responsive echo pulse. The time interval between the receipt of the two mentioned pulses, i.e. the pulse width of the produced timing gate signal, is responsive to the workpiece acoustic velocity.

The method of determining the workpiece acoustic velocity from the timing gate signal pulse width has presented difficulties in the prior art apparatus. For instance, when analog circuits are used to determine the acoustic velocity a constant current generator and a ramp generator are required. Such an arrangement has led to problems in maintaining stable linearity of the waveform with varying operating temperatures and aging of the electronic circuit components.

In other prior art apparatus, a digital circuit is used which provides improved drift and stability characteristics in comparison with the analog circuits, but requires the use of a stable high frequency clock. The high frequency clock tends to produce noise in the circuit and consumes excessive power. For instance, in order to obtain a velocity resolution of 1 m/sec when measuring an aluminium workpiece 25 mm thick, a clock having a frequency in the order of 700 MHz is required. Moreover, for measuring the acoustic velocity of workpieces having different thicknesses, the clock frequency must be changed correspondingly and expensive tuning components exhibiting stable characteristics over a certain temperature range are required. Alternatively, a plurality of high frequency clocks, each oscillating at a different frequency, are required for measuring the acoustic velocity of materials having different thicknesses.

Other prior art systems employ a vernier counting method using two stable, accurate and expensive clock circuits. The method of vernier counting is described in the book, "Pulse, Digital and Switching Waveforms" by Millman and Taub, McGraw-Hill, New York, 1965, pp 683–687.

Time interval averaging is used in certain prior art thickness measuring apparatus. Specifically, in U.S. Pat. No. 3,985,022 issued Oct. 12, 1976 by C. C. DiLeo et al., entitled "Ultrasonic Thickness Measuring Method and Apparatus", a time interval averaging circuit with a programmable means for determining workpiece thickness is described. This patent is incorporated herein by reference.

In the present apparatus, the time interval averaging circuit is modified for use in an acoustic velocity measuring apparatus. Specifically, a programmable number of fixed frequency pulses is counted and accumulated during successive measuring cycles using time interval averaging means until a predetermined quantity of pulses commensurate with the workpiece thickness is counted. Concurrently the quantity of measuring cycles required to accumulate the predetermined quantity of pulses is counted which quantity of measuring cycles is commensurate with the acoustic velocity of the workpiece.

A timing gate signal having a pulse width responsive to the workpiece acoustic velocity is generated as described above. The pulse width is measured by counting the quantity of fixed frequency pulses (P) occurring during each of the timing gate signal interval, dividing the quantity of pulses by a constant N to obtain the average quantity of pulses per measurement (P/N). The quantity of measurements performed (N') typically is made equal to N for obtaining the average quantity of clock pulses counted during the timing gate interval (P) which is:

$$P = P/N \times N'$$

The time interval averaging method described above improves resolutions as compared with the digital measuring method and also provides increased stability by averaging the always present noise to zero. The general time interval averaging system while providing these advantages is not adapted to be calibrated since the quantity of measurements N' in the numerator of the above equation is fixed. In order to maintain the same resolution when measuring workpieces having different thicknesses, a separate clock or an adjustable clock is required for each different thickness, resulting in an expensive and complex apparatus. ONe modification of the basic time interval averaging measurement apparatus for use in an ultrasonic thickness measuring apparatus is described in DiLeo et al supra.

In the present apparatus, a further modification is used for acoustic velocity measurements. A programmable divided by N counter is provided for calibrating the apparatus for measuring the acoustic velocity of workpieces having different thicknesses. In a preferred embodiment the programmable counting means is programmed by suitable indicia bearing means, such as thumb wheel switches, potentiometers or the like, to a value commensurate with the thickness of the workpiece. The quantity of measured pulses P in the above equation is made equal to the value programmed into the programmable counting means. The timing gate signal pulse width is equal to the time required for an ultrasonic signal traveling at an acoustic velocity V to transverse twice the workpiece thickness, i.e. 2 × thickness/velocity. The quantity of pulses per unit of time is equal to the high frequency clock frequency $f$. The fixed value $N$ remains constant so the equation above becomes:

$$P = 2 \times \text{thickness} \times f \times N'/V \times N$$

When the number of pulses counted P is commensurate with the preprogrammed workpiece thickness the equation reduces to:

$$V = 2 \times f \times N' = K \times N'/N$$

Thus, the acoustic velocity (V) is proportional to the number of measuring cycles (N') required for the total count (P) to be equal to the programmed value commensurate with the thickness of the workpiece.

It will be apparent that by proper arithmetic scaling, a readout coupled to a counter which counts the quantity of measurement cycles during a respective velocity measurement will display a value commensurate with the acoustic velocity of the workpiece.

The velocity measuring apparatus can readily be calibrated for measuring the velocity of any workpiece. If the thickness of the workpiece is unknown it may be measured by any known means and the programmable means adjusted to the measured value. For example, a workpiece prior to testing may be conveyed past a thickness gage, the output of the gage being coupled directly to the address means of the programmable counter.

The apparatus described comprises the advantages of the prior art devices without the disadvantages. Since the apparatus employs digital circuits, the inherent disadvantages of the analog circuits are obviated. The programmable means which varies the quantity of pulses counted during a measuring cycle before displaying the acoustic velocity makes it possible to use a single clock at a fixed frequency, wherein the frequency of the clock is lower than that used in many prior digital measuring apparatus.

The velocity measuring apparatus in accordance with the present invention can be used for measuring the velocity of workpieces having different thicknesses without the necessity for changing the clock frequency. Moreover, the heretofore troublesome problems of stability and drift are eliminated.

A principal object of this invention, therefore is the provision of an ultrasonic velocity measuring apparatus comprising a programmable means for use with a time interval averaging circuit.

Another principal object of this invention is the provision of an ultrasonic velocity measuring apparatus including means for measuring workpieces having different thicknesses.

A further object of this invention is the provision of a digital ultrasonic velocity measuring apparatus having programmable means for providing an apparatus characterized by ease of calibration for any desired workpiece thickness and increased stability and resolution.

Further and still other objects of this invention will become more readily apparent when considering the following description in conjunction with the accompanying drawing.

BRIEF DESCRIPTION OF THE DRAWING

The sole FIGURE is an electrical schematic block diagram of a preferred embodiment of the ultrasonic velocity measuring apparatus in accordance with the present invention.

DETAILED DESCRIPTION OF THE INVENTION

Referring to the FIGURE, a repetition rate clock 10 cyclically provides timing pulses, typically at a frequency in the range between 500 Hz and 20 kHz to a pulser 12 for cyclically energizing the transmit-receive probe 14. Alternatively, the clock 10 can provide pulses at a rate other than at a fixed frequency, i.e. at an aperiodic rate, for instance, the clock circuit described in United States patent application Ser. No. 763,865, filed Jan. 31, 1977, by P. Renzel, entitled "Method and Apparatus for Improving the Speed of Ultrasonic Pulse-Echo Testing" may be used. The probe 14 responsive to the electrical signal from the pulser 12 transmits an ultrasonic search pulse into a workpiece W whose acoustic velocity is to be measured and receives echo responsive pulses. These echo responsive pulses are converted by the probe to electrical signals and fed to a receiver circuit 16 which provides echo responsive trigger signals to the timing gate circuit 18 for generating a velocity responsive timing gate signal which corresponds to the transmit time of a respective search pulse traveling at a velocity V through twice the workpiece thickness. There is one timing gate signal produced for each search pulse provided from the probe 14.

A clock 20 provides a train of pulses to a gate circuit 22 at a predetermined frequency. The timing gate signal from the timing gate circuit 18 causes the gate circuit 22 to be open for a time interval commensurate with the width of the timing gate signal. Programmable counting means 24, in a preferred embodiment a fixed divide by N counter circuit, is coupled to the output of the gate circuit 22 for counting the quantity of pulses received from clock 20 via open gate 22 during the respective timing gate signal intervals and accumulating such counts until a preprogrammed quantity of counts, as determined by address means 26, is accumulated. The address means 26 preferably has indicia thereon to facilitate adjustment to a position corresponding to the known workpiece thickness.

A further counter 28 connected to the clock 10 counts the quantity of trigger pulses provided to pulser 12. When the accumulated count in programmable counting means 24 is equal to the preprogrammed quantity per address 26, an update circuit 32 responsive to the signal from counting means 24 causes the count in counter 28 to be displayed in readout 34. A short time later, a signal from delay 30 provides a reset signal to counter 28.

DESCRIPTION OF OPERATION

The address means 26, for example thumbwheel switches are set to an index commensurate with the known thickness of the workpiece. Alternatively, a thickness measuring gage upstream from the test location measures the workpiece thickness and provides a signal commensurate with the measured thickness value to address 26.

For measuring the acoustic velocity of a workpiece, the transmit-receive probe 14 is coupled to the workpiece in acoustic energy transmission contact via a suitable couplant, such as oil or water.

The trigger pulses conducted from repetition rate clock 10 to the pulser 12 cause the pulser 12 to energize the probe 14. Responsive to each applied pulse signal the probe 14 transmits an ultrasonic energy pulse into the workpiece and receives corresponding echo pulses from the entrant surface and rear wall of the workpiece. The received echo signals are converted by the probe 14 into electrical signals and conducted to the receiver 16. The receiver 16 provides output trigger pulses to the timing gate circuit 18. A signal is provided from the repetition rate clock 10 to the timing gate circuit 18 for resetting the timing gate circuit 18 at the start of each cycle. The video output trigger pulse from receiver 16 corresponding to the entrant surface responsive echo signal starts the timing gate circuit 18, and the video output trigger pulse corresponding to the rear wall responsive echo signal stops the timing gate circuit 18. The pulse width of the resultant output timing gate signal is responsive to the distance traveled by the ultrasonic pulse signal through the workpiece during time interval between the trigger signals.

Alternatively, the timing gate circuit 18 may be started by a signal from repetition rate clock 10 delayed a fixed time interval commensurate with the time required for the search pulse to travel through a delay line interposed between the probe 14 and the workpiece surface. The start signal occurs at the time an entrant surface echo responsive signal would be received at the timing gate circuit 18. The use of such artificial start circuits is well known in the art.

The resulting timing gate signal from timing gate circuit 18 is conducted to one input of the gate circuit 22 for opening the gate 22 during the interval when the timing gate signal is present. The clock 20 provides discrete clock pulses to the other input of gate 22. The clock pulse frequency in a preferred embodiment is 12.8 MHz which frequency is much higher than the frequency of the trigger pulses from repetition rate clock 10. During the timing gate signal interval when the gate 22 is open, the clock pulses from the clock 20 are conducted via the open gate 22 to the programmable counting means 24. In a preferred embodiment the programmable counting means 24 comprises a fixed divide by N counter which accumulates one count after receipt of N pulses from clock 20. In the preferred embodiment the value of N is selected to be 256.

It will be apparent that the timing gate signal from timing gate circuit 18 is asynchronous with the clock pulses from clock 20. That is, the opening and the closing of the gate 22 is not coincident with the clock pulses from the clock 20. The quantity of counts counted and accumulated by the counting means 24 therefore varies for each timing gate signal depending upon the point in time at which the timing gate signal occurs in relation to the clock pulse from clock 20. The programmable counting means 24 provides a single count for each N pulses during a respective timing signal interval. It is the asychronous timing of the signals which provide the averaging in the time interval averaging measurement arrangement described.

Concurrently, counter 28 receives and counts the quantity of trigger pulses, and hence, the quantity of measuring cycles required for the programmable counting means 24 to accumulate a count commensurate with the predetermined count in address 26 which count, in turn, is commensurate with the workpiece thickness. Upon accumulating the predetermined quantity of counts a signal is conducted to update circuit 32 and delay 30. The update circuit 32 provides a signal to readout 34 which displays a value commensurate with the quantity of trigger pulses counted by counter 28. By the inclusion of proper scaling circuits in readout 34 the displayed value equals the acoustic velocity of the workpiece. A further signal, delayed in time, from delay 30 resets counter 28 prior to commencement of the next measuring cycle.

To reiterate, the quantity of fixed frequency pulses occurring during each timing gate signal interval is counted by a programmable counting means using time interval averaging techniques. The process is repeated during successive timing gate intervals until the accumulated quantity of pulses counted during each measuring cycle is equal to a predetermined programmed quantity selected to be commensurate with the thickness of the workpiece. Concurrently, a second counter counts the quantity of measuring cycles. When the programmable counting means accumulates the predetermined quantity of counts, the second counter contains a count equal to the quantity of measuring cycles which is commensurate with the acoustic velocity of the workpiece.

While in the foregoing description the signal from counter 28 is provided to a display readout 34, it will be apparent however, that the output signal may be provided to other indicating or display means or to signal processing means. Moreover, the output signal may be used for activating an accept-reject circuit in a nodularity tester where the nodularity of a cast iron workpiece is proportional to the acoustic velocity of the workpiece. That is, a cast iron workpiece having an output signal from counter 28 between set levels is accepted and passed for further processing while another workpiece having an output signal from counter 28 outside the set levels is rejected and returned for further processing.

In an alternative embodiment the receiver 16 or the timing gate circuit 18 may be inhibited for a fixed period of time after the transmission of a search pulse into the workpiece as is known in the art to inhibit the timing gate circuit 18 until after the search signal enters the workpiece to be responsive only to a pair of echo signals arising from rear wall reflections received after the entrant surface signal.

While there has been described and illustrated a preferred embodiment of the present invention and several modifications thereof, it will be apparent to those skilled in the art that further modifications and variations may be made without deviating from the broad principle of this invention which shall be limited solely by the scope of the appended claims.

What is claimed is:

1. An apparatus for measuring the acoustic velocity of a workpiece which includes means for providing trigger pulses, circuit means for transmitting responsive to said trigger pulses an ultrasonic search pulse into the workpiece and subsequently receiving an echo pulse responsive to the transmitting of the search pulse and such search pulse intercepting an acoustic impedance change, means coupled to said circuit means for providing counts commensurate with the transit time of the search pulse traversing the workpiece dimension as determined by a first signal responsive to the transmitting of said search pulse and a second signal responsive to the receipt of the echo pulse, the improvement comprising:

first counting means coupled to said means coupled to said circuit means for counting and accumulating said counts until a predetermined quantity of counts, which quantity is commensurate with the thickness of the workpiece, is accumulated and providing an output signal when such accumulated count is obtained, and second counting means coupled for receiving said trigger pulses and said output signal and counting the quantity of trigger pulses and providing a signal commensurate with the acoustic velocity of the workpiece responsive to receipt of said output signal.

2. An apparatus for measuring as set forth in claim 1, and readout means coupled to said second counting means for receiving said signal commensurate with the acoustic velocity of the workpiece and being conditioned thereby.

3. An apparatus for measuring as set forth in claim 2, said readout means being a digital display.

4. An apparatus for measuring as set forth in claim 1, said means for providing trigger pulses providing said trigger pulses at an aperiodic rate.

5. An apparatus for measuring as set forth in claim 1, said first counting means being programmable by adjustable means.

6. An apparatus for measuring as set forth in claim 1, and readout means coupled to said first counting means and said second counting means for displaying said signal commensurate with the acoustic velocity responsive to receipt of said output signal.

7. An apparatus for measuring the acoustic velocity of a workpiece by the ultrasonic pulse-echo method comprising:
   first clock means for providing trigger pulses;
   pulse generating means coupled for receiving said trigger pulses and providing in response thereto signals causing the transmission of search pulses into the workpiece;
   receiver means coupled for receiving an echo responsive signal in response to the transmission of a respective search pulse;
   timing gate means coupled for receiving a first signal responsive to the transmission of a search pulse and for subsequently receiving a second signal responsive to the echo responsive pulse associated with said search pulse and generating a timing gate signal commensurate with the acoustic velocity of said search pulse in the workpiece during the time interval between said first and second signals;
   second clock means for providing periodic clock pulses;
   programmable counting means coupled for receiving said periodic clock pulses and said timing gate signal for counting and accumulating the quantity of periodic clock pulses occurring during successive timing gate signals and providing a third signal when the accumulated count equals a predetermined quantity commensurate with the thickness of the workpiece;
   counting means coupled for receiving said trigger pulses and providing a fourth signal commensurate with the quantity of trigger pulses counted, and
   readout means coupled to said counting means and said programmable counting means for providing responsive to said third signal said fourth signal commensurate with the acoustic velocity of the workpiece.

8. An ultrasonic apparatus as set forth in claim 7, and means coupling said timing gate means to said first clock means for resetting said timing gate means responsive to said trigger pulses.

9. An ultrasonic apparatus as set forth in claim 7, said programmable counting means comprising a gate coupled to said second clock for receiving at a first input said periodic clock pulses and coupled to said timing gate means for receiving at a second input said timing gate signal, said periodic clock pulses passing through said gate during the time said timing gate signal is manifest at the second input.

10. An ultrasonic apparatus as set forth in claim 9, said programmable counting means comprising further a divide by N counter coupled to said gate for providing said third signal.

11. An ultrasonic apparatus as set forth in claim 7, said programmable counting means comprising an address means and a programmable divide by N counter.

12. An ultrasonic apparatus as set forth in claim 11, said address means comprising settable switches.

13. An ultrasonic apparatus as set forth in claim 7, said readout means being a digital display.

14. An ultrasonic apparatus for measuring as set forth in claim 7, and transducer probe means adapted for being coupled to a workpiece coupled to said pulse generating means and said receiver means.

15. An ultrasonic apparatus for measuring as set forth in claim 14, said first signal being an entrant surface responsive echo signal and said second signal being a rear wall responsive echo signal.

16. An ultrasonic apparatus as set forth in claim 7, said first signal being a rear wall responsive echo signal and said second signal being a subsequent rear wall responsive echo signal.

17. The method of measuring the acoustic velocity of a workpiece by the ultrasonic pulse-echo method comprising:
   providing trigger pulses;
   transmitting responsive to said trigger pulses ultrasonic search pulses into the surface of the workpiece and receiving an echo pulse responsive to each such search pulse intercepting an acoustic impedance change;
   accumulating counts commensurate with the transit time of respective search pulses traversing the workpiece dimension from said surface to the impedance change as determined by the time interval between a first signal responsive to the transmission of such search pulse and the receipt of a second signal responsive to the echo pulse associated with the respective search signal until the accumulated count equals a predetermined quantity commensurate with the thickness of the workpiece, and
   counting the quantity of said trigger pulses during said accumulating such quantity being commensurate with the acoustic velocity of the workpiece.

18. The method of measuring as set forth in claim 17, said predetermined quantity being programmable by adjustable means.

19. The method of measuring as set forth in claim 17, said first signal being responsive to the search pulse entering the surface of the workpiece and said second signal being responsive to said search pulse intercepting the rear wall of the workpiece.

20. The method of measuring as set forth in claim 17, said first signal being an electrical signal generated a predetermined time after transmitting said trigger pulse and said second pulse signal being responsive to an echo signal arising from the rear wall of the workpiece.

21. The method of measuring as set forth in claim 17, said first signal being responsive to said search signal intercepting the rear wall of the workpiece and said second signal being responsive to said search signal subsequently intercepting the rear wall of the workpiece.

22. The method of measuring as set forth in claim 17, said predetermined quantity being programmable in units of thickness.

* * * * *